United States Patent [19]

Kotowski

[11] 4,366,382

[45] Dec. 28, 1982

[54] X-RAY LINE SCAN SYSTEM FOR USE IN BAGGAGE INSPECTION

[75] Inventor: Andreas F. Kotowski, Covina, Calif.

[73] Assignee: Scanray Corporation, Harbor City, Calif.

[21] Appl. No.: 185,561

[22] Filed: Sep. 9, 1980

[51] Int. Cl.³ .............................................. G01N 23/00
[52] U.S. Cl. ......................................... 378/57; 378/99
[58] Field of Search ................... 250/358 R, 359, 360, 250/363 R

[56] References Cited

U.S. PATENT DOCUMENTS

| | | | |
|---|---|---|---|
| 3,780,291 | 12/1973 | Stein et al. ...................... | 250/363 R |
| 3,808,444 | 4/1974 | Schneeberger et al. ........ | 250/358 X |
| 3,884,816 | 5/1975 | Takahashi ......................... | 250/359 |
| 4,031,545 | 6/1977 | Stein et al. ...................... | 250/358 R |
| 4,242,583 | 12/1980 | Annis et al. ..................... | 250/360 X |

*Primary Examiner*—Davis L. Willis
*Attorney, Agent, or Firm*—Edward A. Sokolski

[57] ABSTRACT

A baggage system which employs a fan-shaped x-ray beam which scans baggage on a conveyor belt and produces images of the contents of the baggage on a video monitor. The output of an x-ray source is collimated into a narrow linear beam. Objects to be scanned are exposed to this beam with successive slices of the object being so exposed as the conveyor moves the object past the beam. A light emitting screen receives the beam after it has passed through the object and emits a light pattern in accordance with the characteristics of the object being scanned. The light output of the screen is received by an array of photodetectors which generate electrical signals in accordance with the intensity of the light received thereby. The outputs of the photo-detectors are sequentially sampled to provide a series of signals in accordance with the photo-detector outputs. These signals are converted to digital form and stored in a memory. The output of the memory is fed through appropriate video output circuits to a video monitor where an image of the object being scanned is displayed.

8 Claims, 6 Drawing Figures

X-RAY LINE SCAN SYSTEM FOR USE IN BAGGAGE INSPECTION

This invention relates to x-ray scan systems for inspecting the contents of baggage moving on a conveyor belt, and more particularly to such a system in which the x-rays are collimated into a narrow linear beam such that successive portions of the object are scanned as the conveyor moves such objects past the beam.

The inspection of baggage at airports has now become almost universally mandatory as a safeguard against the hazards of aircraft highjacking. In order to minimize the time involved in such inspection and to provide for a more accurate and efficient inspection without the need for opening baggage, x-ray scan systems have been developed in which x-rays are passed through baggage as it is moved on a conveyor past the x-ray beam and the rays which have passed through the baggage appropriately processed for display on a video monitor to provide images of the contents of the baggage. Such systems have been in use for a number of years. One problem which has been encountered with such systems is that even with very low levels of x-ray radiation, damage can be caused to photographic film and other articles which are highly sensitive to x-ray radiation. Thus, while the average amount of radiation to which such radiation sensitive articles are exposed with systems of the prior art is only of the order of 1 milli-Roentgen, this still is enough radiation to cause damage thereto. To avoid this problem, efforts have been made to lower the radiation. However, with lowered radiation, the signal/noise ratio of the output signal is lowered which results in a significant deterioration of the definition of the video monitor display which is unacceptable for proper baggage inspection. One particular solution to this problem involves the use of a flying spot scanner in conjunction with a mechanical chopper which provides a pulsating beam to which the object is exposed, thereby concentrating the beam yet lowering the average radiation on the object. This, it has been found, lowers the radiation without significantly affecting the quality of the video display, but it has the disadvantage of the expense and inherent reliability problems encountered with a mechanical chopper. In addition, a large portion of the output of the x-ray generator is dissipated in the chopper and not employed in the beam, making for relatively inefficient use of the available x-ray energy.

The device of the present invention obviates the shortcomings of the prior art by providing means for lowering the average radiation to which the object is exposed to a level at which damage to photographic film and other x-ray sensitive articles is avoided (radiation lowered to the order of 0.15 milli-Roentgens). This end result is achieved without the need for any mechanical implementation, such as a mechanical chopper or the like, and with a relatively efficient utilization of the available x-ray radiation.

In achieving the desired end results, the system of the present invention employs means for collimating the output of the x-ray source into a linear beam. This beam is directed towards objects to be inspected as they pass along a conveyor belt. The beam collimation is achieved by means of collimator plates between which radiation from the x-ray source is permitted to pass. After the x-ray beam is passed through the object to be scanned, it strikes against a light-emitting screen in the form of a strip. The light output of the screen is received by a linear array of photo-detectors, the individual outputs of which are appropriately integrated and fed to a sampling circuit. The sampling circuit effectively time multiplexes the integrated photo-detector outputs into a single output having successive pulses representing each of the integrated photo-detector outputs in sequence. These sequential outputs are converted to digital form and stored in a memory from where they are fed to video output circuits for display on a video monitor. In this manner, the radiation to which the objects are subjected is reduced to a very low level (of the order of 0.15 milli-Roentgens) at which level damage to photographic film and other x-ray sensitive articles is obviated. This end result is achieved without any significant depreciation in video monitor picture quality.

It is therefore an object of this invention to lower the x-ray radiation in a baggage inspection system without significantly depreciating picture quality.

It is another object of this invention to provide an improved x-ray inspection system employing a line scan x-ray beam wherein the radiation to which objects are subjected is substantially decreased, and having improved picture quality.

Other objects of the invention will become apparent as the description proceeds in connection with the accompanying drawings of which.

Figure 1:
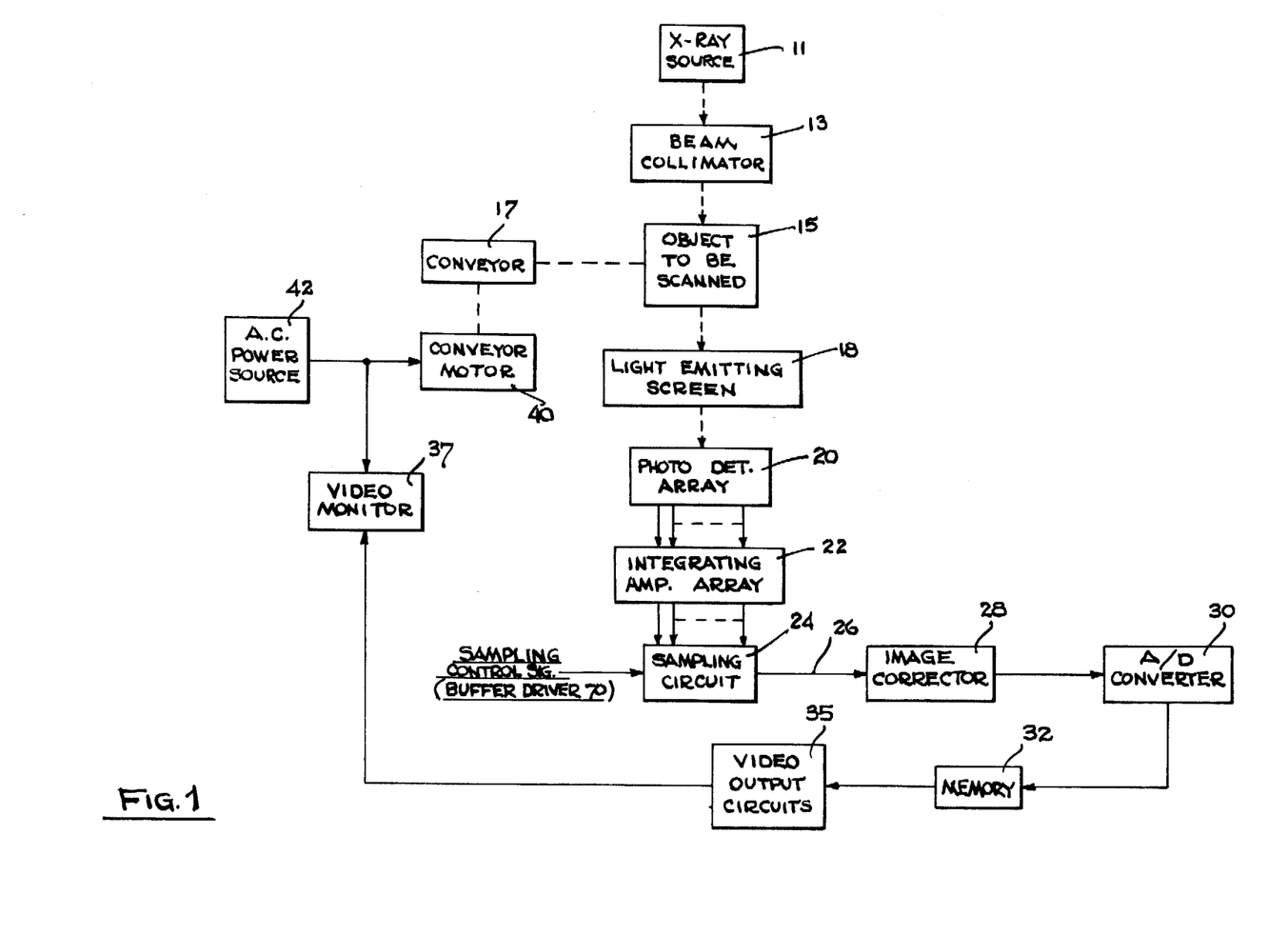
FIG. 1 is a functional block diagram of a preferred embodiment of the invention.

Referring now to FIG. 1, a functional block diagram of the preferred embodiment of the invention is shown. X-ray energy generated by x-ray source 11 is collimated into a linear beam by means of beam collimator 13 which may, as to be explained in connection with FIG. 2, comprise a slot formed between a pair of metal plates. The beam which is collimated into a relatively narrow fan-shaped strip is radiated through an object to be scanned 15 which is moved normal to the strip by means of a conveyor 17 on which the object is supported. Thus, successive "slices" of the object are scanned in sequence by the beam as the conveyor belt moves such objects past the beam. After the x-ray energy has passed through the object, it strikes against a light emitting (phosphor) screen 18 of the type normally employed in x-ray displays. Placed opposite the light emitting screen 18 is a photo-detector array 20, the photo-detectors being arranged in a line directly opposite the screen. The photo-detectors generate electrical outputs in accordance with the light energy impinging thereon, the output of each photo-detector being fed to a corresponding integrating amplifier in integrating amplifier array 22.

The outputs of the amplifiers of integrating amplifier array 22 are fed to sampling circuit 24 which time multiplexes the individual signals received from each of the integrating amplifiers so as to provide a sequential series of pulses on line 26, each such pulse having an amplitude corresponding to that of one of the integrating amplifier outputs. A conventional memory operating in conjunction with a sequential readout circuit may be employed. The signals on line 26 are fed to image corrector 28 which operates to correct diode gain and dark current variations for each of the amplifiers in amplifier array 22, as to be explained further on in the specification. The output of image corrector 28 is fed to analog/digital converter 30 wherein the signal is converted to digital form and in such digital form fed from the analog/digital converter to memory 32. Memory 32 stores the successive "slices" of the object being scanned so that they can be properly displayed on video monitor 37, the output of the memory being fed to video output circuits 35 and from the output circuits to the monitor. Power for conveyor motor 40, as well as video monitor 37, is supplied from a common AC power source 42 so that the mechanical scanning afforded by movement of the conveyor can be appropriately synchronized (through the video output circuits) with the scan circuits of the video monitor.

Figure 2:
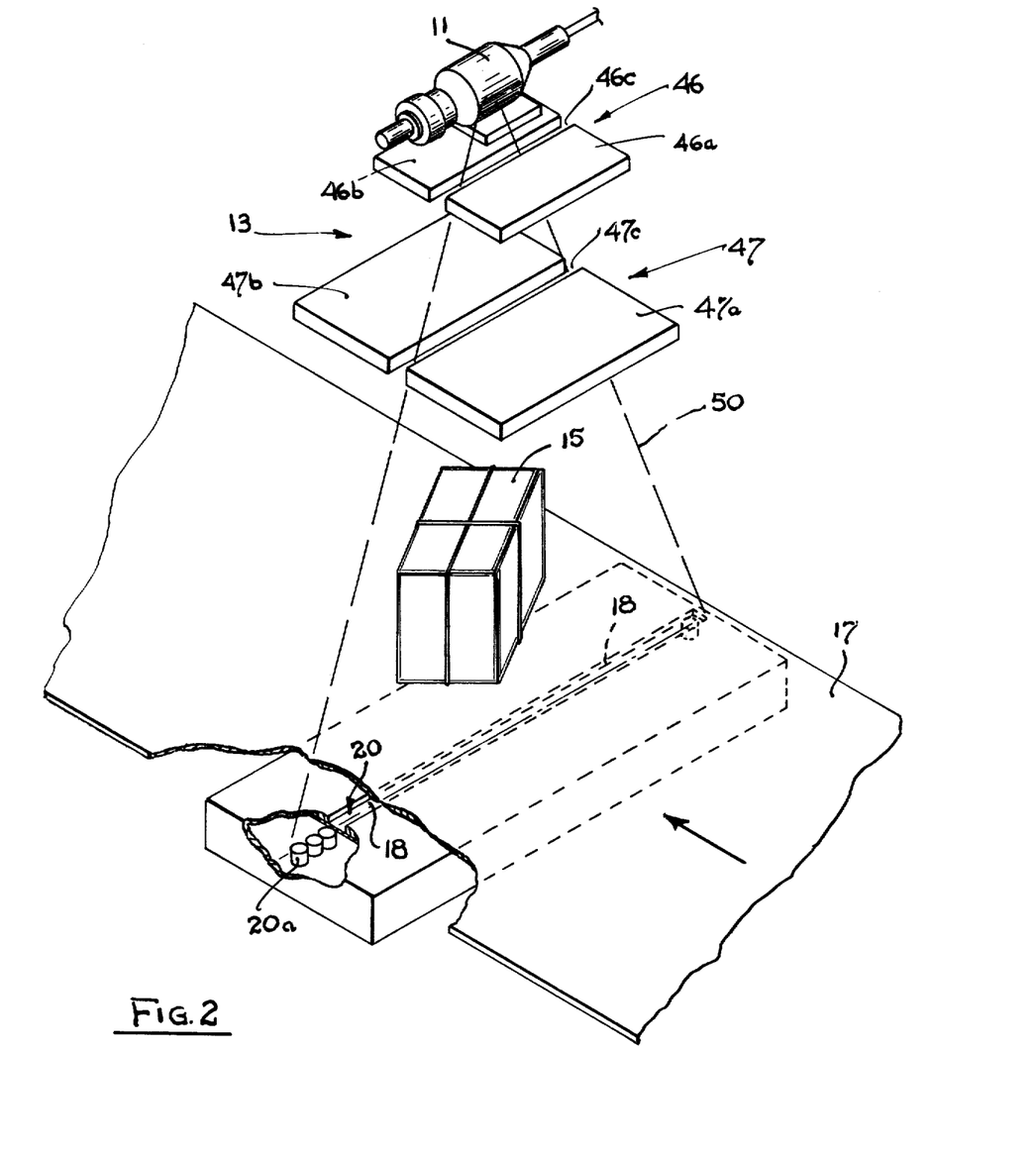
FIG. 2 is a schematic perspective drawing illustrating the system of the invention.

Referring now to FIG. 2, a schematic pictorial representation of a preferred embodiment of the system of the invention is shown. X-ray tube 11 is appropriately mounted in a suitable housing, to provide x-ray radiation towards precollimator and collimator plates 46 and 47, respectively. Collimator plates 46 and 47 are metal plates constructed of a material suitable for shielding x-rays, such as steel. Both the collimator and the precollimator are formed from pairs of plates 46a and 46b and 47b, respectively, these plates being separated from each other by slots 46c and 47c. The widths of slots 46c and 47c are preadjusted to produce a fan-shaped x-ray beam 50 having a width or thickness of $\frac{1}{8}"-1/16"$ in the preferred embodiment. The exact width to which the beam is adjusted is dictated by the resolution requirements of the system. Beam 50 passes through an object to be scanned 15 and then strikes against light-emitting screen 18 which is a conventional x-ray screen of suitable phosphorescent material in the form of a strip corresponding in width to the width of beam 50 (i.e., $\frac{1}{8}'-1.16"$ in width).

The object 15 is supported on conveyor belt 17 which moves successive portions of the object through beam 50 such that successive slices of the object are scanned by the beam. Mounted opposite light emitting screen 18 is a photo-detector array 20 which may comprise a linear array of photo-diodes 20a positioned alongside screen 18. In an operative embodiment of the invention, screen 18 and the diode array 20 are approximately 30 inches in length with approximately 500 photo-diodes forming the array. When x-ray photons strike x-ray screen 18, screen 18 emits light in accordance with the energy in each such photon and the number of photons which is dependent upon the characteristics of the portion of the object 15 through which the photon has passed. Thus, the light emitted by various portions of screen 18 is in accordance with the characteristics of object 15 being scanned. The photo-diodes 20a receive light from the portions of the screen thereopposite and each photo-diode generates an electrical current in accordance with the intensity of the light signal received thereby.

As already noted in connection with the explanation of FIG. 1, the output of each of photo-diodes 20a is amplified in a corresponding integrating amplifier and after time multiplexing and image correction has been accomplished converted to digital form and placed in a memory for display on a video monitor.

Figure 3:
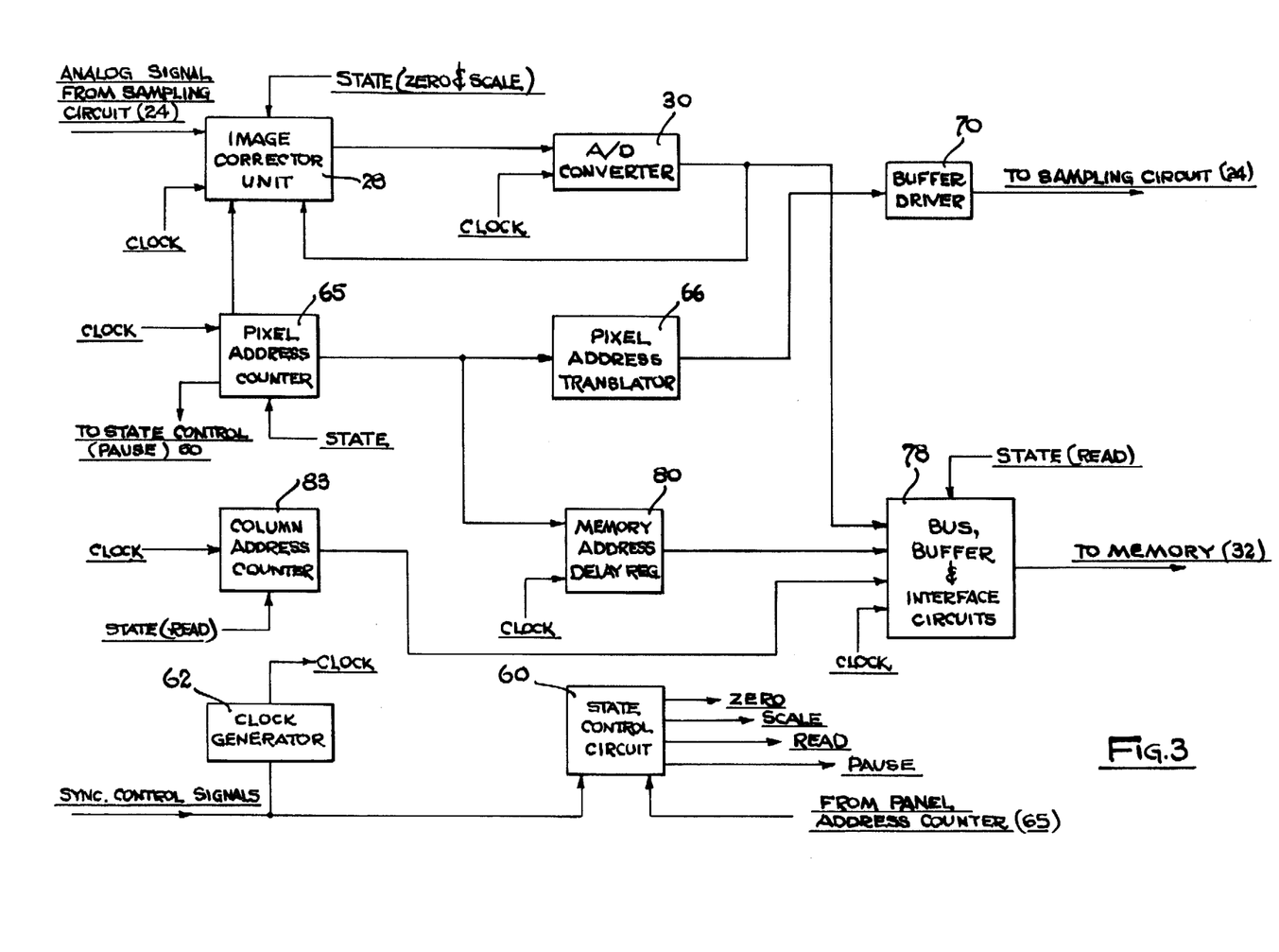
FIG. 3 is a functional block diagram illustrating the video processing and control circuitry of the preferred embodiment.

Referring now to FIG. 3, the video processing and control circuitry of the preferred embodiment is schematically illustrated. The basic function of this circuitry is to accept the signal output generated by the photo-detector array 20 which represents an image of the objects being scanned, and to store this information in memory so that it can be appropriately displayed on a video monitor. In the preferred embodiment, the circuitry, on command, scans a vertical column of 480 pixels (one pixel for each diode in the detector array) and then stops, this operation being successively repeated until all of the vertical columns making up the desired picture have been scanned. In its operation, various portions of the circuitry are selectively placed in one of four separate states by means of state control circuit 60. This circuit may have four control flip-flops in its output circuit which are driven to the "1" state in response to sync control signals fed to the state control circuit. The four states controlled by the "ZERO", "SCALE", "READ" and "PAUSE" outputs of state control circuit 60 represent: (1) a "0" operation during which the "0" offsets of the detectors are measured and recorded; (2) a scale operation during which the full-scale brightness value of the detectors are measured and recorded; (3) a read operation during which the brightness values of the outputs of the detectors (representing the images of the objects being scanned) are measured and stored in a memory; and (4) a pause operation between successive read operations during which the circuits are reset for a succeeding operation. It is to be noted that the operation of the four states is independent and all operations can be either simultaneous or sequential as the command signals may dictate. Synchronization signals for timing the operating of the circuits is provided by clock generator 62 which is synchronized with the sync control signals.

Upon receiving a command signal for a read operation from state control circuit 60, pixel address counter 65 is loaded with a number corresponding to the number of photo-diodes and proceeds to count down to zero at predetermined timing intervals. Pixel address counter provides an address representing each of the diodes to pixel address translator 66, which translates this address signal into proper format for driving the diode sampling circuit 24 (FIG. 1). Thus, the output of pixel address translator 66 drives buffer driver 70 which in turn provides a control signal for the diode sampling circuit so as to cause the sequential sampling of the diode outputs in turn in accordance with the output of the pixel address counter 65.

The signal corresponding to the sampled output of each of the photo-diodes is fed to image corrector unit 28 which operates to correct the signal in accordance with the gain and offset of each selected photo-diode. The detailed operation of image corrector unit 28 will be described further on in the specification in connection with FIG. 4. The output of image corrector unit 28 is converted from analog to digital form by analog/digital converter 30. The output of analog/digital converter 30 is fed to bus, buffer and interface circuits 78 which provide the input and control for the memory units 32 (FIG. 1). The pixel address signal is fed from pixel address counter to bus, buffer and interface circuits 78 through memory address delay register 80 which operates to delay the address by one sampling cycle of the diodes, this to match the delay in the sampling operation.

Column address counter 83 provides a signal to bus, buffer and interface circuits 78 which in conjunction with pixel address counter 65 determine the location in the memory of any pixel in the displayed image.

When the pixel counter reaches "0", indicating that all of the diode outputs have been sampled, the circuits are driven to a "pause" state by the output of the "pause" output of state control circuit 60. The pixel address counter then resets itself to the full count representing the number of diodes (480 in the illustrative embodiment) so that it is ready for a succeeding operation.

At the end of each read operation, column address counter 83 is either incremented or decremented by "1", depending on the direction in which the column scanning is going, i.e., from the left to right or right to left.

Figure 4:
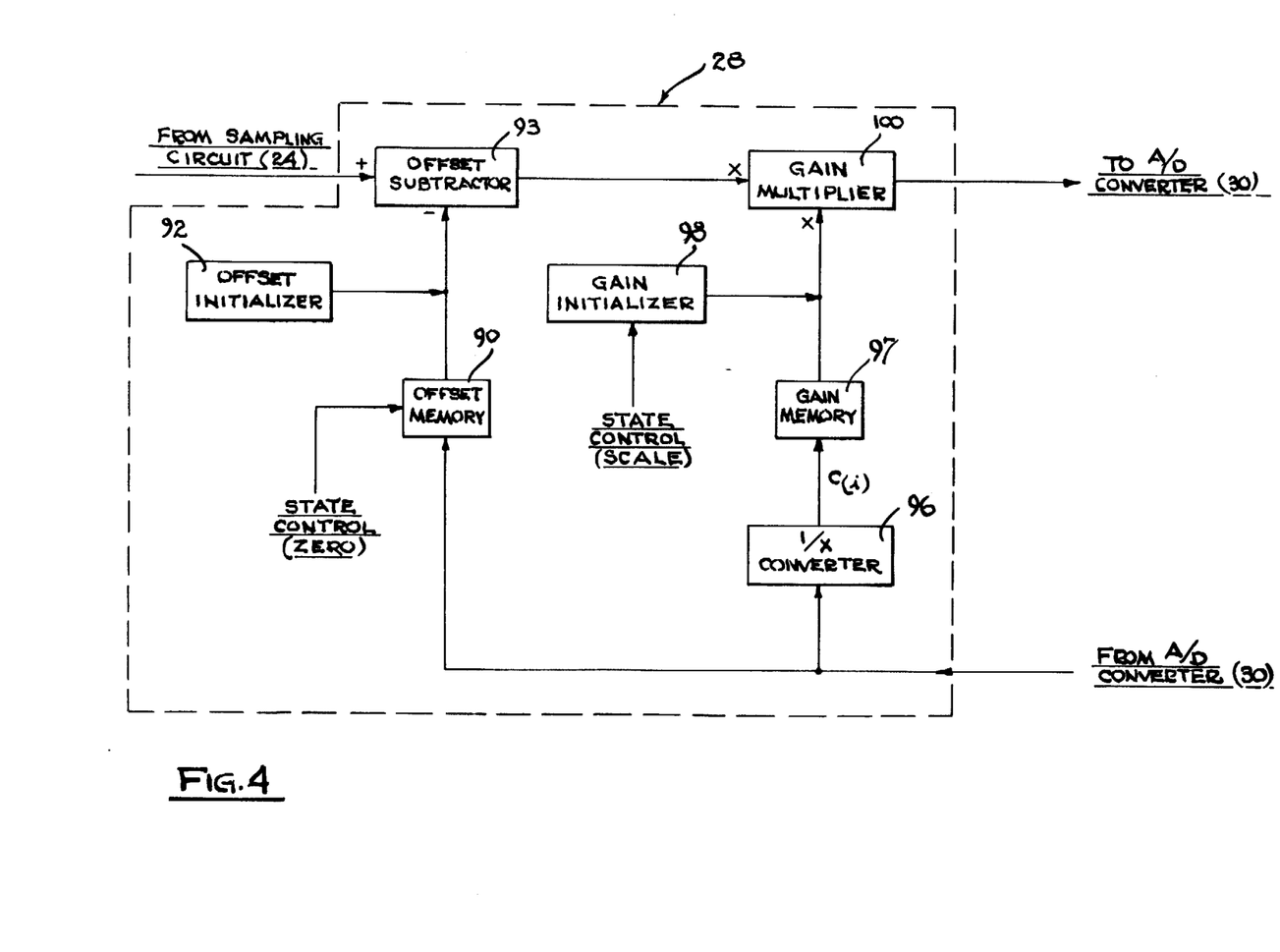
FIG. 4 is a functional block diagram illustrating the circuitry of an image corrector unit employed in the preferred embodiment.

Referring now to FIG. 4, the operation of the image corrector unit is illustrated. As has already been noted, such correction is needed to correct the photo-detector outputs to compensate for individual gain and offset differences. A correction signal for each of the photo-detector outputs is periodically read into memory circuits for use to effectively compensate the output of each diode in accordance with the measured offset and gain thereof. Such calibration may be made as often as the situation may demand. In the preferred embodiment, such calibration is automatically programmed whenever there is a time interval of two seconds or more between objects passing through the x-ray beam. When the output of state control circuit 60 is simultaneously commanding "ZERO" and "SCALE" operations, the image corrector unit functions to generate the desired correction signal. During this time, the x-ray generator is automatically turned off by the control circuits for the measurement of offset.

The signal, $S_{(i)}$, from each of the photo-diodes is as follows:

$$S_{(i)} = I_{D(i)} + G_{(i)}B_{(i)} \quad (1)$$

where:

$I_{D(i)}$ is the dark current (or offset) of the photo-diode
$G_{(i)}$ is the x-ray conversion gain of the photo-detector
$B_{(i)}$ is the brightness (or x-ray intensity) at the photo-detector To perform its function, the image corrector must correct $S_{(i)}$ to produce $SC_{(i)}$ where $SC_{(i)}$ is the direct analog of the brightness $B_{(i)}$. This can be defined as follows:

$$SC_{(i)} = \frac{S_{(i)} - I_{D(i)}}{G_{(i)}} = B_{(i)} \quad (2)$$

A problem is presented, however, in the measurement of $I_{D(i)}$ and $G_{(i)}$, as the values of these parameters can change with temperature and time. To solve this problem, these parameters are measured periodically and stored in a RAM. $I_{D(i)}$, the offset of the photo-diode, is measured by reading $S_{(i)}$ with the x-ray source turned off such that:

$$S_{(i)} = I_{D(i)} + G_{(i)} \cdot \phi = I_{D(i)} \quad (3)$$

During zero operations, these offset values are stored in offset memory 90. Also during this operation, offset initializer 92 operates to set offset subtractor 93 to "0".

The gain, $G_{(i)}$, of each diode is measured by reading the signal from each diode $S_{(i)}$ with the x-ray source turned on and no object in the path of the x-ray beam. At this time, all the brightness values, $B_{(i)}$, correspond to full white. By subtracting the already measured offset $I_{D(i)}$ stored in offset memory 90, the gain, $G_{(i)}$, of each diode may be measured, as indicated by the following equation:

$$\begin{aligned}S_{(i)} &= I_{D(i)} + B_{(i)}G_{(i)} - I_{D(i)} \\ &= B_{(i)}G_{(i)}\end{aligned} \quad (4)$$

In view of the fact that there is no object in the x-ray beam, $B_{(i)}$ is equal to "1" and therefore $S_{(i)} = G_{(i)}$.

The arithmetic inverse of the diode gain $G_{(i)}$ is calculated by means of the 1/X converter 96 which is implemented with an ROM look-up table. The output of 1/X converter 96 is a gain correction factor, $C_{(i)}$, which is stored in gain memory 97. During scale operation, gain initializer 98 sets a gain factor of ¼ into gain multiplier 100 which multiplies the output of the gain memory by this factor when it is fed to analog/digital converter 30. The gain setting is so reduced to avoid saturation of the photo-detectors during the scale operation. Other gain factors could be used but it has been found in the preferred embodiment that a factor of ¼ operates quite satisfactorily. In this manner, offset errors and gain differences in the diodes are compensated for so that they will not affect the imaging.

The operation of the system of the invention is summarized as follows: The array is scanned with the x-ray beam off. The dark current for each diode is read, 0.0 is subtracted, the value is multiplied by ¼, converted to digital form, and finally stored in the appropriate spot in the offset memory. When all dark currents have been stored, the x-ray beam is turned on. Without any parcel in the x-ray beam, the array is scanned a second time. The full-scale signal current is read from each diode, the offset of that diode subtracted, the value multiplied by ¼, converted to digital form, and stored in the appropriate spot in the gain memory.

In operation, the array is continuously scanned. Each signal value read from the diodes is first corrected for dark current, and then for diode gain before being converted to a digital number stored in memory.

Figure 5A:
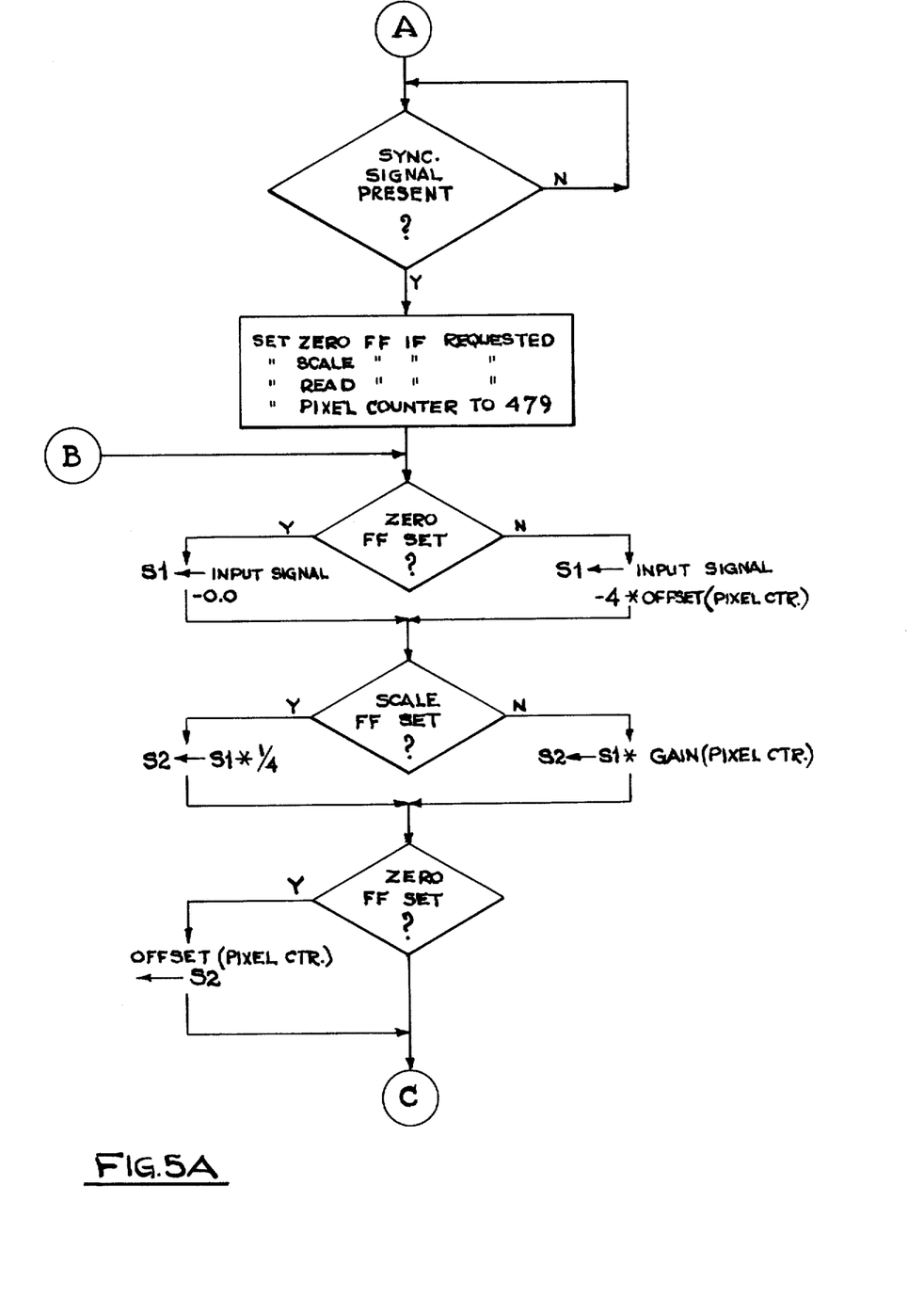
FIGS. 5A and 5B are flow charts defining the operation of the preferred embodiment.
Figure 5B:
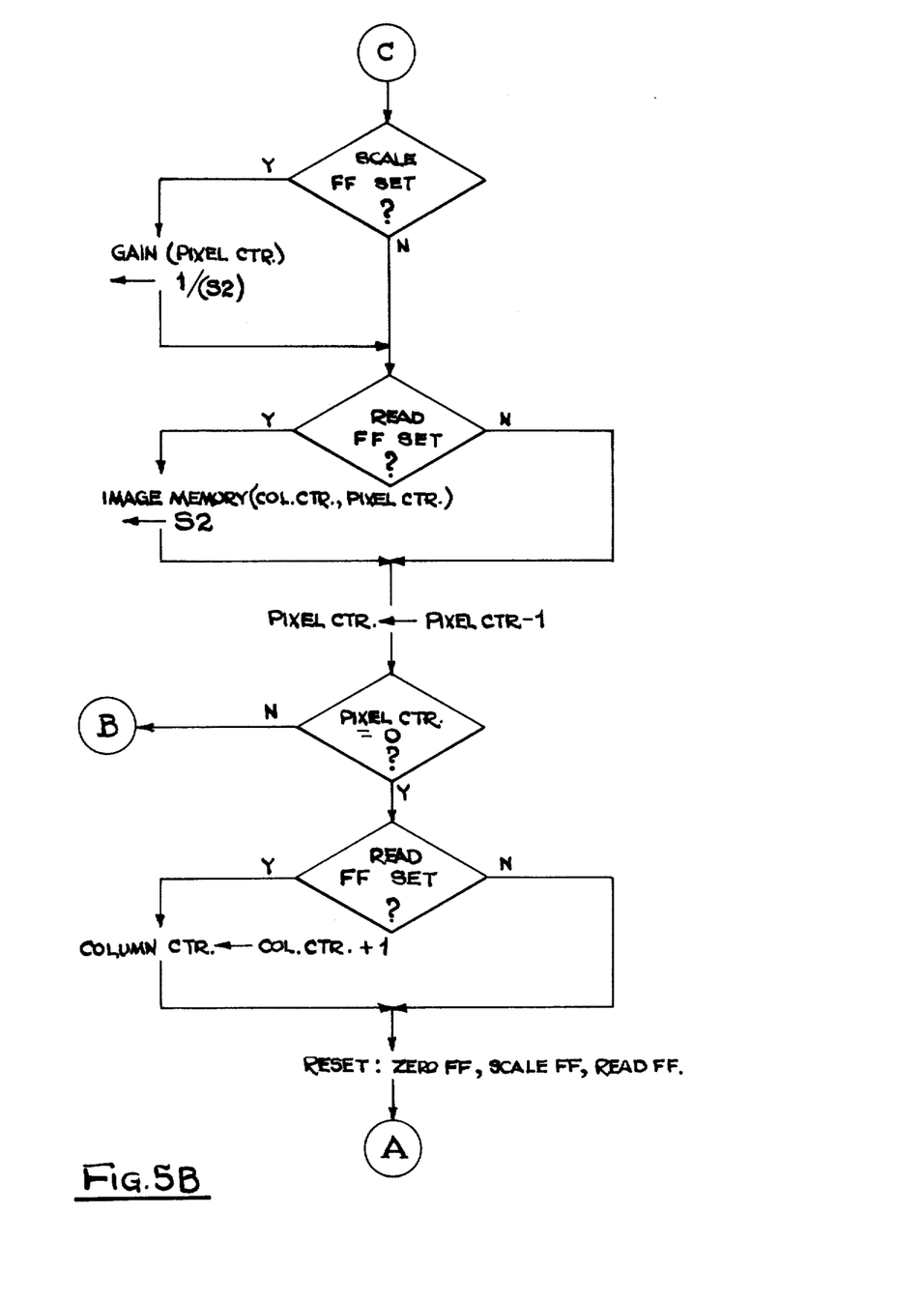

The flow chart of FIGS. 5A and 5B more precisely defines the operation of the preferred embodiment. The various terms used in the flow chart are defined as follows:

| | |
|---|---|
| Sync — | Signal starting each input scan line. Sync synchronizes scanning to conveyor motion. |
| Zero FF — | Flip flop indicating that a zero operation is in progress (when set). During a zero operation the offset currents of the photo-diodes are individually measured and stored in the offset memory. |
| Scale FF — | Flip flop indicating that a scale operation is in progress (when set). During a scale operation the signal level representing white (full brightness) of each diode is measured. A gain correction factor which is the inverse of the white level is stored in the gain memory for each diode. |

-continued

| | |
|---|---|
| Read FF — | Flip flop indicating that a read operation is in progress (when set). During a read operation brightness values (from the sensor) are stored in the Image Memory. |
| Input Signal — | Signal for the current level of the presently selected photo-diode. The diode selected is determined by the Pixel Counter. |
| S1 — | Signal after offset correction has been applied. |
| S2 — | Signal after gain correction has been applied. |
| Offset — | Memory holding 480 offset values corresponding to the offset currents of the photodiodes. Offset (i) represents the stored offset of the $i^{th}$ photo-diode. |
| Gain — | Memory holding 480 gain correction values corresponding to the inverse (1/X) of the full brightness levels of the photo-diodes. Gain (i) represents the stored gain correction for the $i^{th}$ photo-diode. |
| Image Memory — | A memory array storing one complete television frame. The image is stored as an array of picture elements (pixels). Image memory (X,Y) indicates the pixel (picture element) in column X and line Y where: $0 \leq X \leq 511$ and $0 \leq Y \leq 479$. |
| Pixel Counter — | Counter counting pixels in a column. Counter determines which photo-diode is selected. |
| Column Counter — | Counter counting columns in an image. Used only to address the image memory. |

It is to be noted that the system of the invention can also be used for non-destructive testing and for inspection of materials and products such as, for example, food, manufactured products, etc.

While the invention has been described and illustrated in detail, it is to be understood that this is by way of example only and is not to be taken by way of limitation, the spirit and scope of the invention being limited only by the terms of the following claims.

I claim:

1. A system for inspecting objects including
    an x-ray source,
    conveyor means for moving said objects through rays in the output of said source,
    means for receiving said rays after they have passed through said objects,
    means responsive to the output of said receiving means for providing a video display in accordance with the receiving means output comprising a light-emitting screen in the form of a strip, an array of photo-detectors opposite said screen for generating electrical signals in accordance with the light emission of the portions of the screen thereopposite, separate means for individually integrating the output of each of said detectors, electronic sampling circuit means for time multiplexing the outputs of said integrating means to provide a series of sequential pulses representing the outputs of said integrating means, means responsive to said pulses for generating video output signals, and video monitor means responsive to said video output signals for displaying said video output signals, and
    means for collimating the rays of said source into a narrow fan-shaped beam prior to their passage through the objects, said beam scanning said objects in successive slices as the conveyor means moves the objects therethrough.

2. The system of claim 1 wherein said collimating means comprises at least a single pair of plates spaced from each other by a predetermined distance to form a slot therebetween, the width of the beam being determined by the spacing between the plates.

3. The system of claim 2 wherein said collimating plate means comprises a first pair of precollimator plates and a second pair of collimator plates in series with the first pair of plates, the plates of each of said pairs of plates being spaced from each other by a predetermined distance to form a slot therebetween, the width of the beam being determined by the spacings between said pairs of plates.

4. The system of claims 1 or 2 wherein each of said integrating means comprises a diode and further including image corrector means receiving the output of said multiplexing means for periodically correcting diode gain and dark current variations in each of said diodes.

5. The system of claim 4 and further including state control circuit means for setting said system into a plurality of different operating states including "ZERO" and "SCALE" states for use in operating said image corrector means to correct diode gain and dark current variations.

6. The system of claim 1 wherein said means for generating video output signals includes analog/digital converter means for converting the multiplexed output to digital form, memory means for storing the output of the analog/digital converter means, and video output circuit means responsive to the output of the memory for providing display signals to said video monitor means.

7. The system of claim 6 and further comprising means for sequentially reading out the pixels representing outputs of each of said diodes into said memory.

8. The system of claim 7 and further including means for sequentially reading out columns of the pixels representing outputs into said memory.

* * * * *

US004366382B1

REEXAMINATION CERTIFICATE (2778th)
United States Patent [19]
Kotowski

[11] B1 4,366,382
[45] Certificate Issued Jan. 23, 1996

[54] X-RAY LINE SCAN SYSTEM FOR USE IN BAGGAGE INSPECTION

[75] Inventor: Andreas F. Kotowski, Covina, Calif.

[73] Assignee: Scanray Corporation, Harbor City, Calif.

Reexamination Requests:
No. 90/003,708, Jan. 31, 1995
No. 90/003,947, Sep. 11, 1995

Reexamination Certificate for:
Patent No.: 4,366,382
Issued: Dec. 28, 1982
Appl. No.: 185,561
Filed: Sep. 9, 1980

[51] Int. Cl.⁶ ................................................. G01N 23/00
[52] U.S. Cl. ................................................ 378/57; 378/98.8
[58] Field of Search ............................. 378/51, 57, 62, 378/98.7, 98.8, 147, 146

[56] References Cited

U.S. PATENT DOCUMENTS

| | | | |
|---|---|---|---|
| 3,558,809 | 1/1971 | Aoki. | |
| 3,800,078 | 3/1974 | Cochran et al. | 178/7.1 |
| 3,856,989 | 12/1974 | Weimer | 178/7.1 |
| 3,922,091 | 11/1975 | Suva et al. | |
| 3,936,630 | 2/1976 | Blossfeld | 250/211 J |
| 3,952,144 | 4/1976 | Kolker. | |
| 3,995,164 | 11/1976 | Ramsay et al. | |
| 4,041,315 | 8/1977 | Hounsfield | 250/360 |
| 4,051,458 | 9/1977 | Morton | 340/146.3 AG |
| 4,052,620 | 10/1977 | Brunnett. | |
| 4,053,774 | 10/1977 | Berdahl. | |
| 4,072,289 | 2/1978 | Brueckner et al. | |
| 4,090,080 | 5/1978 | Tosswill. | |
| 4,095,107 | 6/1978 | Genna et al. | |
| 4,134,683 | 1/1979 | Goetz et al. | 356/407 |
| 4,138,721 | 2/1979 | Boyd | 364/414 |
| 4,158,505 | 6/1979 | Mathisen et al. | 356/308 |
| 4,172,659 | 10/1979 | Laska | 355/68 |
| 4,179,100 | 12/1979 | Sashin | 250/416 TV |
| 4,320,296 | 3/1982 | Ishida et al. | |
| 4,341,956 | 7/1982 | Bax. | |

OTHER PUBLICATIONS

"A Survey of X–Ray Technology and Available Systems for Parcel Inspection," Cumings, 1979 Carnahan Conference on Crime Countermeasures, University of Kentucky, May 16–18, 1979 (pp. 117–122).

"A X–Ray Inspection System for Security Screening Applications," Stefanski et al., Proceedings 1977 International Conference on Crime Countermeasures—Science and Engineering, University of Kentucky, Jul. 25–29, 1977 (pp. 57–64).

Sashin et al., "Computer Electronic Radiography for Early Detection of Vascular Disease," Proceedings of the Society of Photo–Optical Instrumentation Engineers, vol. 173, Toronto, Ont., Canada, Mar. 1979, pp. 88–97.

Stefanski et al., "An X–Ray Inspection System for Security Screening Application," Picker Canada Ltd., Montreal, Quebec, Canada, pp. 57–64.

*Primary Examiner*—David P. Porta

[57] ABSTRACT

A baggage system which employes a fan-shaped x-ray beam which scans baggage on a conveyor belt and produces images of the contents of the baggage on a video monitor. The output of an x-ray source is collimated into a narrow linear beam. Objects to be scanned are exposed to this beam with successive slices of the object being so exposed as the conveyor moves the object past the beam. A light emitting screen receives the beam after it has passed through the object and emits a light pattern in accordance with the characteristics of the object being scanned. The light output of the screen is received by an array of photodetectors which generate electrical signals in accordance with the intensity of the light received thereby. The outputs of the photo-detectors are sequentially sampled to provide a series of signals in accordance with the photo-detector outputs. These signals are converted to digital form and stored in a memory. The output of the memory is fed through appropriate video output circuits to a video monitor where an image of the object being scanned is displayed.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *